(12) United States Patent
Langlotz et al.

(10) Patent No.: US 7,726,171 B2
(45) Date of Patent: Jun. 1, 2010

(54) DEVICE AND PROCESS FOR CALIBRATING GEOMETRICAL MEASUREMENTS OF SURGICAL TOOLS AND ORIENTING THE SAME IN SPACE

(75) Inventors: Frank Langlotz, Zofingen (CH); Urs Rohrer, Kerzers (CH)

(73) Assignee: AO Technology AG, Chur (CH)

( * ) Notice: Subject to any disclaimer, the term of this patent is extended or adjusted under 35 U.S.C. 154(b) by 482 days.

(21) Appl. No.: 11/575,246

(22) PCT Filed: Sep. 15, 2004

(86) PCT No.: PCT/CH2004/000583

§ 371 (c)(1),
(2), (4) Date: Apr. 25, 2007

(87) PCT Pub. No.: WO2006/029541

PCT Pub. Date: Mar. 23, 2006

(65) Prior Publication Data

US 2007/0276357 A1    Nov. 29, 2007

(51) Int. Cl.
*G01B 21/00* (2006.01)
(52) U.S. Cl. ....................................... 73/1.79
(58) Field of Classification Search .................. 73/1.79; 606/1
See application file for complete search history.

(56) References Cited

U.S. PATENT DOCUMENTS

| 5,987,960 | A  | * | 11/1999 | Messner et al. ............... 73/1.79 |
| 6,306,126 | B1 |   | 10/2001 | Moctezuma |
| 2003/0040879 | A1 |   | 2/2003 | Jutras et al. |
| 2004/0039402 | A1 |   | 2/2004 | Zeiss et al. |
| 2004/0167654 | A1 |   | 8/2004 | Grimm et al. |

FOREIGN PATENT DOCUMENTS

| EP | 0904735 | 3/1999 |
| WO | 02061371 | 8/2002 |

* cited by examiner

*Primary Examiner*—Hezron Williams
*Assistant Examiner*—Nashmiya S. Fayyaz
(74) *Attorney, Agent, or Firm*—Rankin, Hill & Clark LLP

(57) ABSTRACT

A device (1) for calibrating geometrical measurements of surgical tools (10) as well as for orienting the same in space, including: A) a docking station (2) having two jaws (3) and a surface (21); and B) at least three marking indicators (9) firmly attached to the docking station (2) and capable of being measured, in reference to their position in space, electromagnetically or acoustically through a position detecting device (14), where C) the jaws (3) each have a lateral wall (40) so that the surface (21) and the lateral walls (21) of the two jaws (3) enclose a U-shaped passage (18), where D) the two jaws are conformed in a cylindrical or double conical manner; and E) the two lateral walls (40) or the surface (21) present a form comprising at least two additional contact points for a surgical tool (10) inserted between the jaws (3) across its longitudinal axis (11).

17 Claims, 4 Drawing Sheets

DEVICE AND PROCESS FOR CALIBRATING GEOMETRICAL MEASUREMENTS OF SURGICAL TOOLS AND ORIENTING THE SAME IN SPACE

BACKGROUND OF INVENTION

1. Field of Invention

The invention refers to a device for calibrating geometric measurements, orienting and positioning of surgical tools in space.

2. Description of Related Art

Such devices are suitable for the calibration of geometric measurements, especially of the diameter, position and/or orientation of surgical tools in space. The calibration of the position and orientation is above all needed for surgical tools employed in computer-assisted surgery, where the position and orientation of various surgical tools is measured, during an operation, while using a surgical navigation system including a position detecting device. Such a navigation system merely allows determining the position of a marking indicator applied to the tool or a machine comprising the tool, for instance a drilling machine. An intra-operative calibration is for instance indispensable for drilling processes where the drill, if inserted into a drilling machine in-situ, is inserted into a position with respect to the drilling machine and the marking indicators which is previously unknown.

A device of this kind is known from the EP-A 0 904 735 MESSNER. This known calibrating device also allows, apart from determining the position of the tip of a tool, measuring the diameter of the tool by using two jaws than can be shifted to each other in a linear manner. Before the measurement, the jaws must be shifted relative to each other so as to precisely contact the mantle surface of the surgical tool along their entire longitudinal axis parallel to the surgical tool. The disadvantage of this known device is that measuring errors may occur if the jaws cannot make proper contact over their entire length.

BRIEF SUMMARY OF THE INVENTION

The invention intends to remedy this situation. The task underlying the invention is to create a device capable of measuring essential geometric measurements, especially the diameter, width and height of longitudinal, prismatic or cylindrical objects having a centrally symmetrical cross section, without requiring a shift of the jaws.

The invention solves the proposed task through a device for calibrating geometric measurements and orienting surgical tools in space that comprises: a docking station having two jaws and a surface; and at least three marking indicators arranged on the docking station in a fixed manner and measurable in reference to their spatial position electromagnetically or acoustically, in order to determine the position and orientation of the device in space through a position detecting device. The jaws are stationary with respect to the surface of the docking station and have one lateral wall each, so that the surface and the lateral walls of the two jaws encompass a U-shaped passage. The two jaws are, at least on the surface portions opposite to each other, conformed in a round cylindrical, hyperboloid or double-cone shaped fashion, so that a surgical tool which has been inserted between the jaws can be laid down on at least one contact point of each jaw across its longitudinal axis. The device further comprises a rotary table with an axis of rotation extending vertically in relation to the surface and two clamping jaws projecting over the surface. And, the two lateral walls or the surface or the rotary table have a form comprising at least two additional points of contact for a surgical tool inserted between the jaws across its longitudinal axis, so as allow a lateral docking, defined with respect to the marking indicators, of a surgical tool passed between the jaws (3).

The advantages secured by the invention are essentially seen in the fact that tanks to the device according to the invention:

- various cylindrical or prismatic surgical tools with a circular or rectangular cross sectional surface can be docked to the docking station in a position defined by the marking indicators;
- cylindrical or prismatic surgical tools having other than circular or rectangular cross sectional surfaces, for instance oval or elliptical cross sectional surfaces, can be docked to the docking station in a position defined by the operator;
- the diameter of round cylindrical objects or the width or height of objects with other cross sectional surfaces can be measured without requiring a shift of the jaws;
- the space orientation of various prismatic or cylindrical surgical tools can be measured;
- because the marking indicators, which are preferably applied on a tool handle, meaning the tool shank at an axial distance, generate a lengthening of the arms encompassing the angle $\alpha$, so that a small change of the angle $\alpha$ creates an additional increase of the distances between the marking indicators on the tool and those on the device, which makes it possible to achieve a precision greater than that with shiftable jaws;
- the jaws are locked to the docking station in an immovable manner, so that while measuring no twisting or jamming can occur.

Other favourable embodiments of the invention are characterized in the subordinate claims.

In a preferred embodiment the jaws are, at least at their opposite surface portions, conformed as double cones and comprise at their axial centre an indentation penetrating across the central axis. The advantage of this conformation is essentially in the fact that the notched portion aids the jaws in positioning an inserted tool in a defined position. The indentations of the jaws are preferably conformed in alignment with each other, whereby the additional effect desirable for a measurement, that of increasing the angle $\alpha$ at increasing diameter, is enhanced because both contact points of the tool are diverging further from the central axes of the jaws.

The indentations are also preferably conformed in the shape of a V and have a depth T across the central axis.

In a further embodiment the device additionally encompasses positioning means suitable for a precise positioning of the front ends of various surgical tools in relation to the docking station. This allows achieving the advantages that the position of the front end, for instance of a drill bit, can be detected by the same device. Moreover, the position of the front end of a tool and its axis can be calibrated in series in successive independent steps. In the device divulged in EP-A 0 904 735 MESSNER, a single working step must guarantee that the tool has been inserted into the calibrating device up to the stop, and that both jaws have properly contacted the tool.

Again in another embodiment, the jaws are spaced from each other between at least 100 mm and 300 mm, so that the great distance of the jaws, when measuring the angle, allow a high degree of precision when calibrating the position of the longitudinal axis of the tool. The jaws are moreover not movable with respect to the docking station.

In one more embodiment the device comprises a rotary table and a axis of rotation extending vertically from the surface, and two clamping jaws are projecting above the surface, so that the surgical tool can be releasable clamped on the rotary table of the device.

In another embodiment the docking station is fitted with a torsion spring, by which the rotary table is pushed in a first rotating direction around the axis of rotation. This allows the torsion spring to press a surgical tool, which has been obliquely inserted among the jaws, against the jaws in a self acting manner and without expending a manual force, or to insert a surgical tool between the jaws in the case of an inversed rotation. It also guarantees that the tool is pressed against both jaws and rests on them in the desired defined position.

The rotary table is preferably movable, through an operating element, against the spring pressure in a second rotating direction around the axis of rotation. This achieves the advantage that the rotary table can, through the operating element, be turned so as to allow inserting a surgical tool between the jaws, or in the case of an inverted rotation, to press it against the jaws. By assisting the one rotating direction by spring pressure and the other by hand pressure, a simple manual handling of the device is assured.

The clamping jaws are preferably arranged on the rotary table so as to be penetrated by a straight line crossing the axis of rotation, whereby at a rotation of the rotary table in a first rotating direction the angle $\beta$ enclosed between the straight line and the reference line is reduced, so that a surgical tool inserted between the jaws can be pressed against the jaws.

In a further embodiment a toothed-wheel gearing is installed between the operating element and the rotary table.

The positioning means preferably include depressions having different geometric shapes and in particular different cross sectional surfaces.

In an additional embodiment the central axes of the jaws are set vertically to the surface. The jaws are also, at least on the surface portions opposing each other, conformed in a round cylindrical manner, while their surface is shaped in a flat manner. This allows attaining the advantage that flat tools, for instance bits or saw blades can be laid down on the surface without causing a twist between the jaws.

The process of calibrating the geometric measurements of surgical tools as well as their orientation in space essentially encompasses the following steps:

A) inserting a surgical tool in a U-shaped passage formed by the surface of the docking station and by the two cylindrical or double cone-shaped jaws belonging to the docking station;

B) turning the surgical tool so as to reduce the angle $\alpha$, which is enclosed by the longitudinal axis of the surgical tool and a reference straight line defined by the shape of the jaws or the shape of the jaws and the surface, to the point that the mantle surface of the surgical tool comes into contact with the lateral walls of the jaws in an orientation defined by the shape of the jaws, or by the shape of the jaws and the surface itself.

C) measuring, through a position detecting device, the spatial orientation of the marking indicators attached to a reference device fastened to the docking station and to a reference device fastened to the surgical tool, D) determining the angle $\alpha$ from the measured positions of all the marking indicators by using a computer; and E) determining the size of the surgical tool, which is vertically extended between the central axes of the jaws, from the measured angle $\alpha$ and the known geometry of the jaws with respect to the marking indicators on the reference device of the docking station through a computer.

In a preferred embodiment the process additionally includes the following steps:

F) inserting the front end of a surgical tool in a depression provided on the docking station, where the position of the bottom of the depression relative to the marking indicators on the reference device on the docking station is already known; and G) measuring the spatial position of the marking indicators, which are attached to the reference device fastened to the docking station and to the reference device fastened to the surgical tool through a position detecting device;

H) determining the spatial position of the front end of the surgical tool from the measured positions of all the indicators through a computer.

The invention and the developments of the invention are in the following explained in further detail by using partially simplified representations of several examples of embodiment.

DETAILED DESCRIPTION OF THE INVENTION

Figure 1:
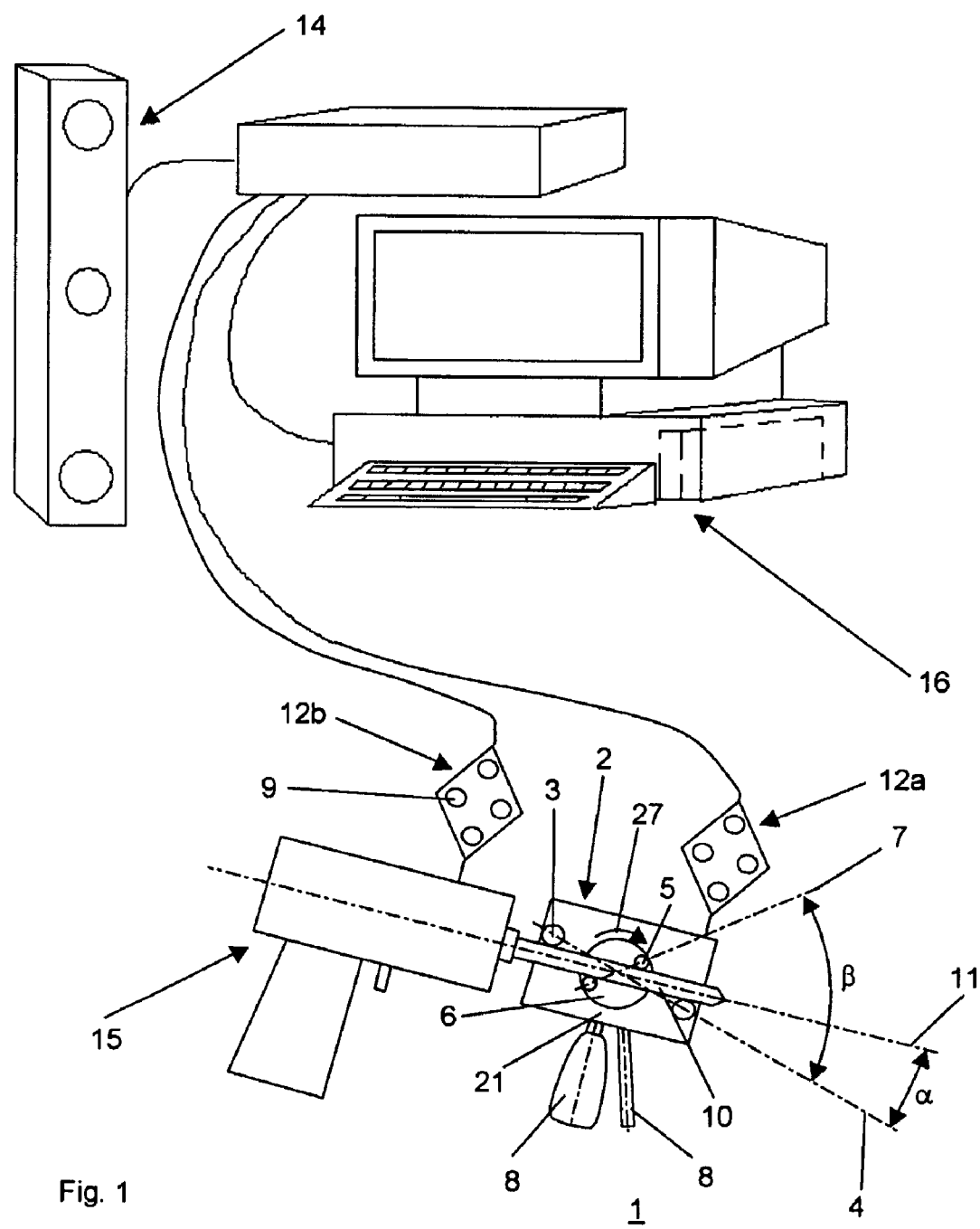
FIG. 1 shows a perspective view of a form of embodiment of the device according to the invention, together with a surgical navigation system.

FIG. 1 shows a form of embodiment of the device 1 which is essentially realized by a docking station 2 fitted with two jaws 3 and a reference device 12a, together with a drill held in a driving machine 15 coaxially to its axis as a surgical tool 10, as well as by a position detecting device 14 and a computer 16. The jaws 3 and the surface 21 encompass a U-shaped passage 18 (FIG. 3) suitable for passing a longitudinal surgical tool 10. The round cylindrical jaws 3 present parallel central axes 24 which are set up centrally to the flat surface 21 of the docking station 2. The surgical tool 10, meaning the drill, is passed through the jaws 3 and rests, through its mantle surface concentric to the longitudinal axis 11, at two points on the jaws 3 and the surface 21, while the longitudinal axis 11 encloses an angle $\alpha$ with one of the reference straight lines 4 crossing the two central axes 24 (FIG. 3) of the jaws 3 at right angles. An additional reference device 12b is provided on the driving machine 15. Both reference devices 12 are fitted with four marking indicators 9 capable of being detected electromagnetically or acoustically, so that the spatial position of the marking indicators 9 can be measured through the position detecting device 14. Based on the measurement of the spatial position of the marking indicators 9, the computer 16 can then determine the position of the longitudinal axis 11 and of the reference straight line 4, as well as the angle $\alpha$ enclosed between them. At a known value of the angle $\alpha$, the known geometries of the two jaws 3 and of the surgical tool 10 allow determining the size of the surgical tool 10, which is in this case conformed as a drill. In case of surgical tools 10 conformed in a different manner, the measurement enclosed between the jaws 3 in a sense vertical to the central axes 24 is taken. The jaws 3 are firmly attached to the docking station 2 and in this case conformed in a round cylindrical fashion. The docking station 2 also includes a rotary table 6 with an axis of rotation 25 extended vertically to the surface 21, which comprises two clamping jaws 5 projecting above the surface 21. The rotary table 6 can, by using the handle 8 firmly attached to the docking station 2, be rotated against the spring pressure of a torsion spring 26 (FIG. 3) around the axis of rotation 25. If the operating lever 17 is not under the action of a force, the rotary table 25 is moved by the force of the torsion spring 26 (FIG. 3) in a first direction of rotation 27, so that the surgical tool 10 passed between the jaws 3 is pressed, by the clamping jaws 5 arranged on the rotary table 6, against the jaws 3. If the operating lever 17 is pressed against the handle 8, the rotary table is moved in the opposite second direction 28, so that a surgical tool 10 can, without being hampered by the clamping jaws 5, be inserted into the docking station 2. The rotary table is in this case conformed in a circular shape concentric to the axis of rotation 25, while the two clamping jaws 5 are arranged in a diagonal direction.

Figure 2:
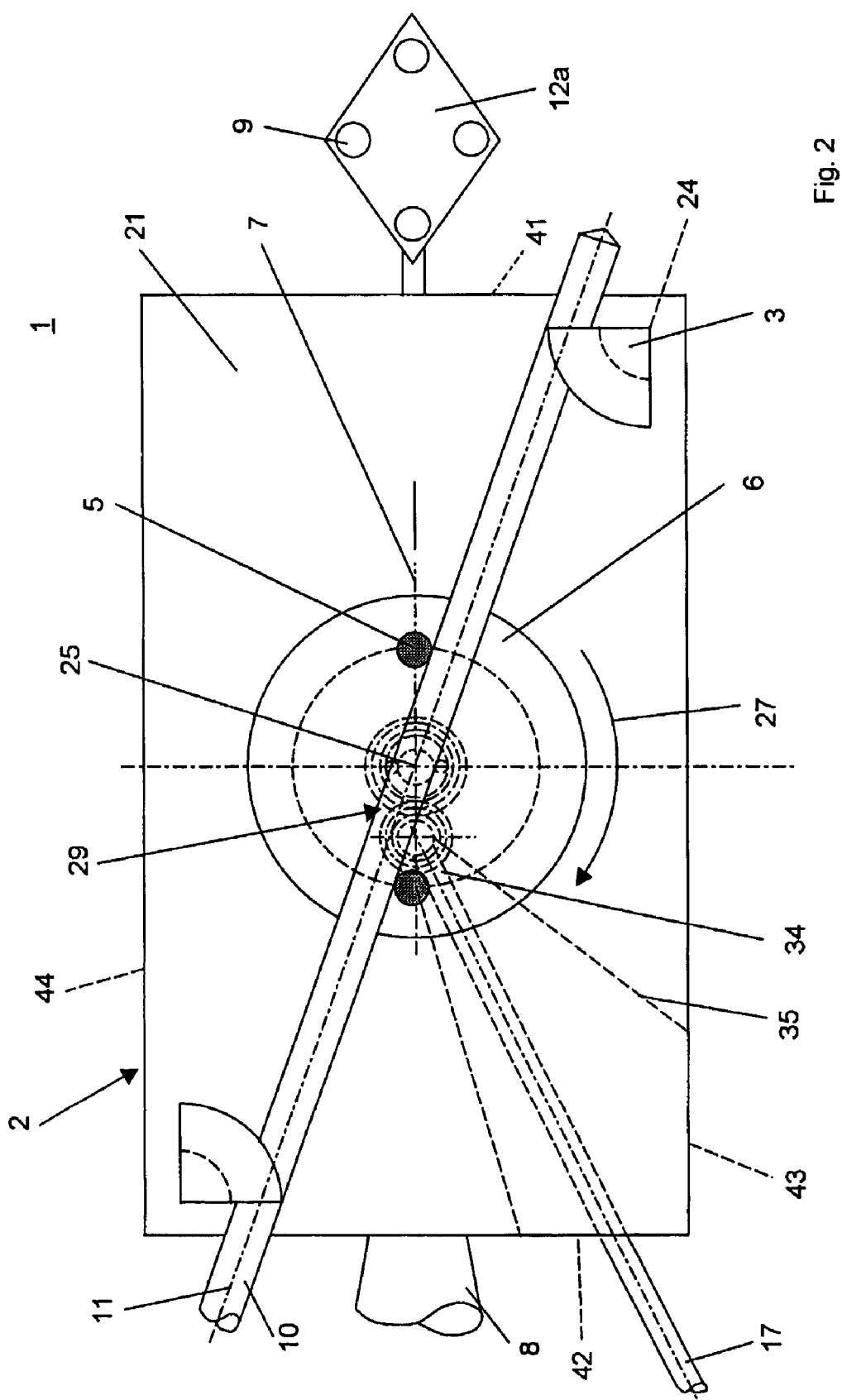
FIG. 2 shows a top view of a form of embodiment of the device according to the invention.
Figure 3:
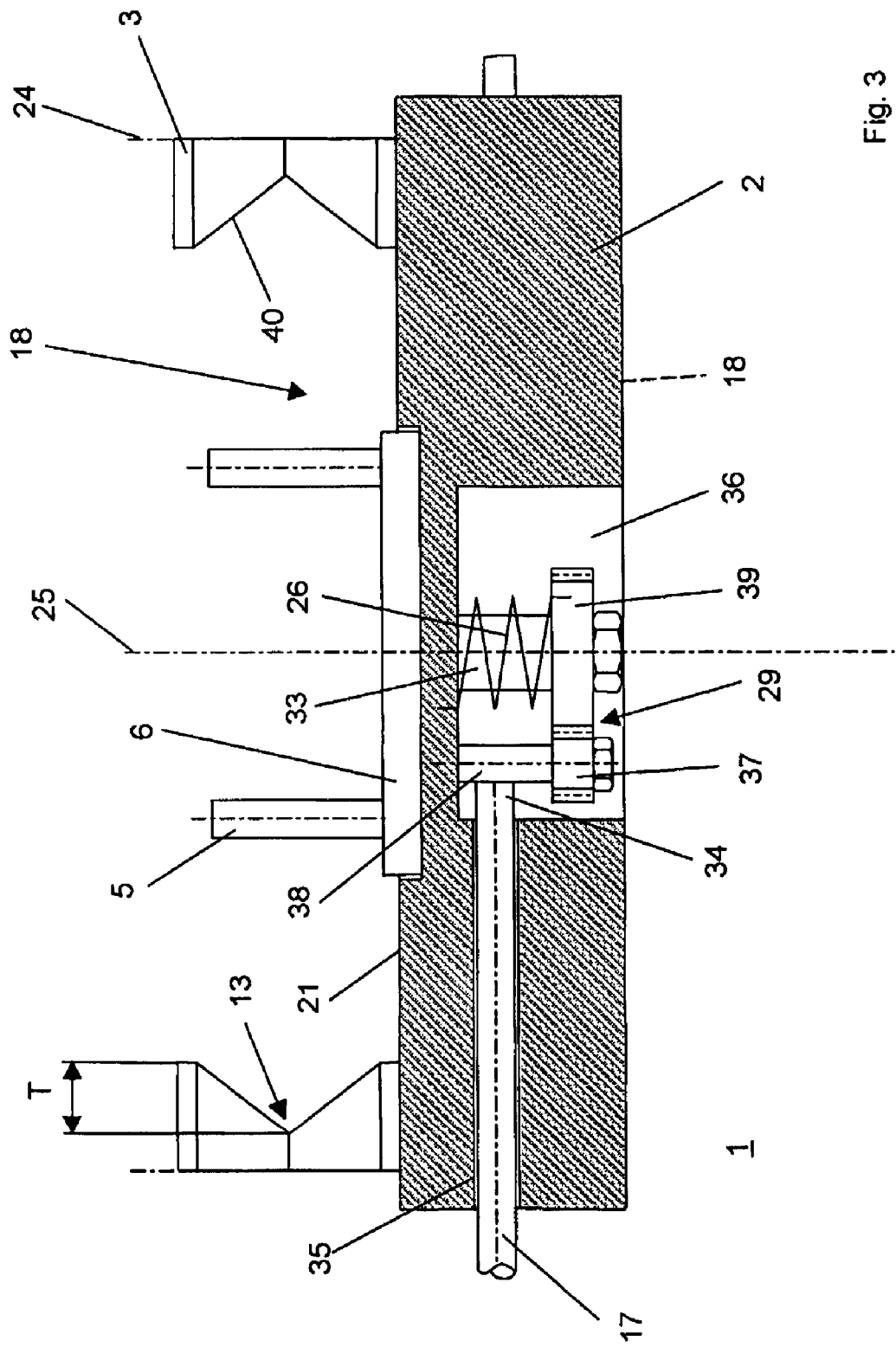
FIG. 3 shows a longitudinal cross section through the form of embodiment of the device according to the invention shown in FIG. 2.

The FIGS. 2 and 3 represent a form of embodiment of the device 1, whose square shaped docking station 2 comprises two jaws 3 set up on the surface 21 in a diagonal direction. The jaws 3 are conformed on the surface portions opposite to each other in a double-conical form, and are thus fitted, at an axially central point, with a V-shaped indentation 13 penetrating into the jaws 3 across the central axes 24, so as to achieve a defined position of a surgical tool 10 against the jaws 3. The central axes 24 are defined by the centres of two conical, circular sector-shaped cross sectional surfaces per jaw 3. The indentations 13 on the lateral walls 40 have, if measured across the central axes 24, a depth T and are aligned with each other. The surgical tool 10 is inserted between the jaws 3 so that its longitudinal axis 11 passes between the jaws 3 and that the mantle surface of the surgical tool 10, which is concentric to the longitudinal axis 11, rests at two points, respectively, inside each of the two indentations 13 on the two lateral walls 40 of the jaws 3. Moreover, a toothed wheel-gearing 29 is disposed between the axis 33 of the rotary table 6 and the front end 34 of the operating lever 17. The docking station 2 pictured here exhibits four lateral surfaces 41;42;43;44, where the reference devices 12 are applied to the first lateral surfaces 41 through four marking indicators 9 capable of being detected electromagnetically or acoustically. The handle 8, along with the operating lever 17, is arranged on the opposite, second lateral surface 42. The operating lever 17 is passed through an opening 35 into the central hollow space 36 which is open against the bottom surface 18 of the docking station 2, and is fastened with its front end 34 to the axis 38 of the first toothed gear 37, which is connected to the docking station 2 in a rotating manner. The first toothed gear 37 is engaged with a second toothed gear 39, which is likewise fastened to the axis 33 of the rotary table 6 which is connected to the docking station 2 in a rotating manner. The axis 33 of the rotary table 6 runs coaxially to the axis of rotation 25 of the rotary table 6 and is set vertically to the surface 21. Two clamping jaws projecting beyond the surface 21 are also arranged on the rotary table 6. The rotary table 6 is conformed on its cross sectional surface set orthogonally to the axis of rotation 25 in a circular manner, while the two clamping jaws 5 are arranged in a diagonal direction. A torsion spring 26 concentric to the axis of rotation 25, which presses the rotary table 6 in a first rotating direction 27, is also arranged between the docking station 2 and the second toothed gear 39. By using the operating lever 8, the rotary table 6 can be moved in the second direction of rotation against the force of the spring. The force of the torsion spring 26 allows achieving the action of moving the rotary table 6 in the first direction of rotation 27, so that the angle β enclosed between the straight line 7 crossing then axis of rotation 25 and centrally penetrating the clamping jaws and the reference straight line 4 (FIG. 1) is reduced, and that a surgical tool 10 inserted between the jaws 3 is pressed against the jaws 3.

Figure 4:
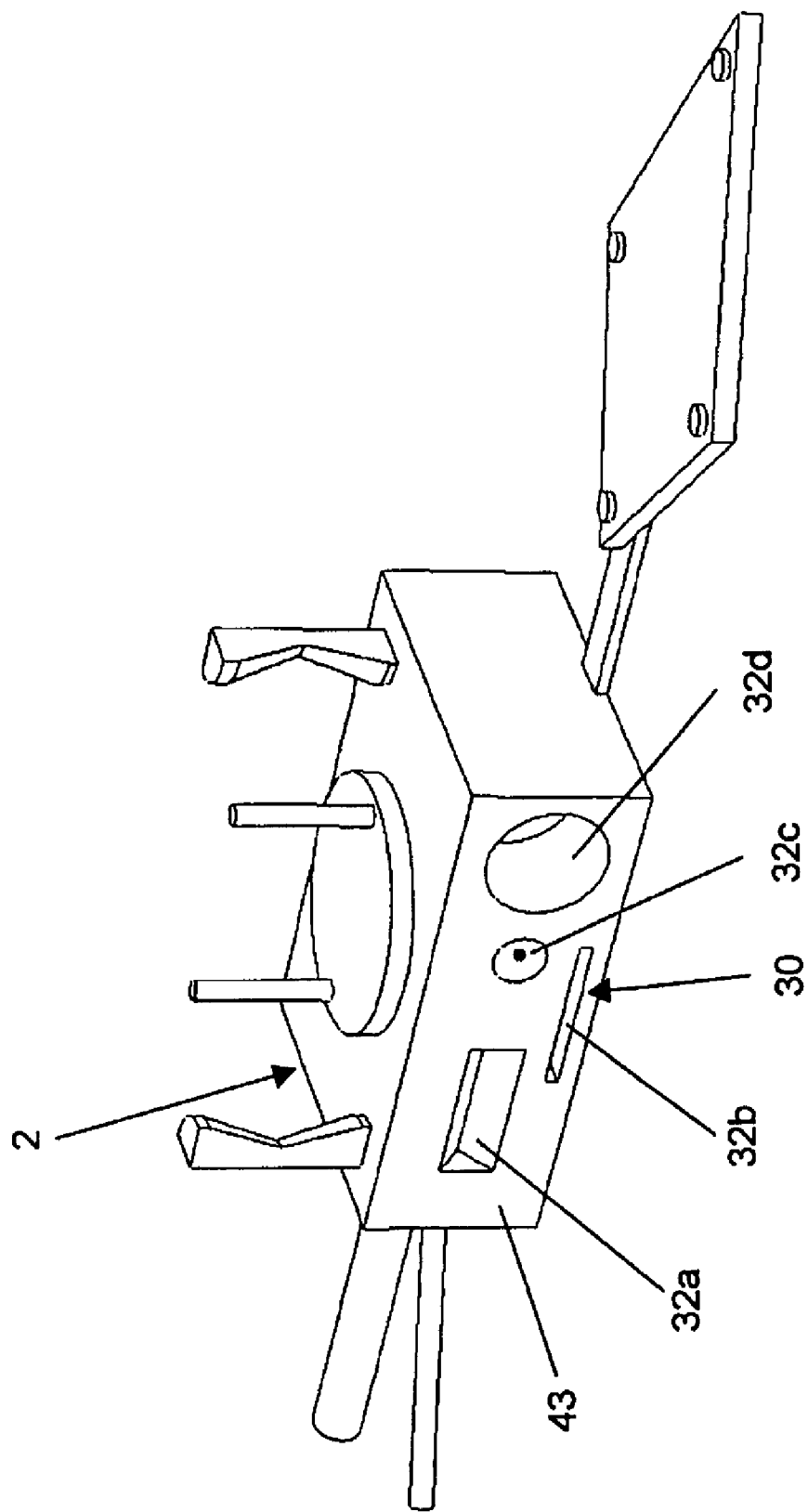
FIG. 4 shows a perspective view of the form of embodiment of the device according to the invention shown in the FIGS. 2 and 3.

FIG. 4 shows a form of embodiment comprising positioning means 30 arranged on a third lateral surface 43 of the docking station 2, so as to position the front ends 31 (FIG. 2) of various surgical tools 10 with respect to the docking station 2. These positioning means 30 comprise depressions 32 having geometries differing from each other for a defined reception of different surgical tools 10 (FIG. 1;2). In particular, the depressions 32a;32b;32c;32d are conformed so that:

The depression 32a presents a rectangular entrance opening parallel to the third lateral surface 43 and tapering from the long sides of the entrance opening toward the bottom of the depression 32a, so as to make it suitable for receiving the front ends of for instance a flat chisel;

The depression 32b is conformed as a slot with a flat bottom of the depression 32b, so as to be suitable for receiving the front end of for instance a saw blade;

The depression 32c is conformed in a conical shape and suitable for centering the tip of for instance a pointer; and The depression 32d is conformed as a round cylindrical borehole with a flat bottom, so as to be suitable for receiving cylindrical tools with various tips.

The invention claimed is:

1. A device (1) for calibrating geometrical measurements of surgical tools (10) and orienting the same in space, the device (1) comprising:
   A) a docking station (2) having two fixed jaws (3) and a surface (21); and
   B) at least three marking indicators (9) arranged on the docking station (2) in a fixed manner, said at least three marking indicators (9) being measurable in reference to spatial position electromagnetically or acoustically through a position detector (14) in order to determine the position and orientation of the device (1) in space,
   C) wherein the two jaws (3) extend perpendicularly from the surface and are locked to the docking station (2) in an immovable manner and thus remain stationary with respect to the surface (21) of the docking station (2) such that the surface (21) and lateral walls (40) of the two jaws (3) define a passage (18) for receiving a surgical tool;
   D) wherein the two jaws (3) are, at least on surface portions opposite to each other, conformed in a round cylindrical, hyperboloid or double-cone shaped fashion such that a surgical tool (10) can be laid down between the two jaws (3) so as to make contact with at least one contact point of each of the two jaws (3) across a longitudinal axis (11) of the surgical tool (10),
   E) wherein the device (1) further comprises a rotary table (6) placed within the surface (21) of the docking station and having two clamping jaws (5) mounted above the surface (21), the rotary table (6) having an axis of rotation (25) that extends vertically from the surface (21) such that the clamping jaws can be rotated with the table to hold the surgical tool; and
   F) wherein the two lateral walls (40) or the surface (21) or the rotary table (6) have a form comprising at least two additional points of contact for contacting a surgical tool (10) inserted between the two fixed jaws (3) across a longitudinal axis (11) of the surgical tool (10), so as allow a lateral docking, defined with respect to the marking indicators (9), of the surgical tool (10).

2. The device (1) according to claim 1, wherein each of the two fixed jaws (3) are, at least on the surface portions opposite to each other, conformed in double-cone shaped fashion and comprise, in an axially central point, a V-shaped indentation (13), and wherein the two fixed jaws (3) each have a central axis (24) defined by centers of circles or partial circles in cross-sections of the double-cone shaped surface portions of the two fixed jaws.

3. The device (1) according to claim 2, wherein the V-shaped indentations (13) of the two fixed jaws (3) have a depth T and are conformed in a manner aligned to each other.

4. The device (1) according to claim 3, wherein an angle $\alpha$ between a reference straight line (4) that penetrates the lateral walls (40) in the V-shaped indentations (13) of the fixed two jaws at the depth T and passes through the central axes (24) of the two fixed jaws and a longitudinal axis (11) of a docked surgical tool (10) is $\alpha<90°$.

5. The device (1) according to claim 1, wherein the device additionally comprises positioning means (30) to position front ends (31) of different surgical tools (10) with respect to the docking station (2).

6. The device (1) according to claim 1, wherein the fixed jaws (3) have a distance from each other of between 100 mm and 300 mm.

7. The device (1) according to claim 2, wherein the central axes (24) of the two fixed jaws (3) are parallel to each other.

8. The device (1) according to claim 1, wherein a torsion spring (26) arranged on the docking station (2) biases the rotary table (6) in a first rotating direction (27) around the axis of rotation (25).

9. The device (1) according to claim 8, wherein the rotary table (6) can be moved through an operating element (8) against the force of the spring in a second direction of rotation around the axis of rotation (25).

10. The device (1) according to claim 8, wherein the clamping jaws (5) are arranged on the rotary table (6) so as to be centrally penetrated by a straight line (7) crossing the axis of rotation (25).

11. The device (1) according to claim 10, wherein rotation of the rotary table (6) in the first rotating direction (27), causes an angle $\beta$ between the straight line (7) and the reference straight line (4) to be reduced, so that the surgical tool (10) inserted between the two fixed jaws (3) can be pressed against the two fixed jaws (3).

12. The device (1) according to claim 9, wherein a toothed-wheel gearing (29) is arranged between the operating element (8) and the rotary table (6).

13. The device (1) according to claim 5, wherein the positioning means (30) comprise depressions (32) having geometries differing from each other.

14. The device (1) according to claim 13, wherein the depressions (32) have different cross sectional surfaces.

15. The device (1) according to claim 1, wherein the surface (21) is conformed in a flat manner and the two fixed jaws (3) are, at least on the surface portions opposite each other, conformed in the round cylindrical fashion.

16. A process for calibrating geometrical measurements of surgical tools (10) as well as for orienting the same in space, comprising the following steps:
    A) inserting a surgical tool (10) into a U-shaped passage (18), formed by a surface (21) of a docking station (2) and two round cylindrical or double cone-shaped jaws (3) that are fixed to the docking station (2);
    B) rotating the surgical tool (10) so that an angle $\alpha$, which is defined between a longitudinal axis (11) of the surgical tool (10) and by a reference straight line (4) defined by the shape of the two jaws (3) or the shape of the two jaws (3) and the surface (21), is reduced to the point that a mantle surface of the surgical tool (10) comes to rest against lateral walls (40) of the two jaws (3) at an orientation defined by the form of the two jaws (3), or the form of the two jaws (3) and the surface (21);
    C) pressing the surgical tool (10) against the two jaws (3) by means of clamping jaws (5) arranged on a rotary table (6) placed within the surface (21) of the docking station and having the two clamping jaws (5) mounted above the surface (21), the rotary table (6) having an axis of rotation (25) that extends vertically from the surface (21) such that the clamping jaws can be rotated with the table to hold the surgical tool;
    D) measuring a spatial position of marking indicators (9) fastened to the docking station (2) and to the surgical tool (10), through a position detector (14);
    E) determining the angle $\alpha$ from the measured positions of the marking indicators (9) fastened to the docking station (2) and to the surgical tool (10) through a computer (16); and
    F) determining a diameter extending vertically to central axes (24) of the two fixed jaws (3) or a width of the surgical tool (10) from the measured angle $\alpha$ and the known geometry of the two fixed jaws (3) with respect to the marking indicators (9) on the docking station (2) through a computer (16).

17. The process according to claim 16, further comprising the following steps:
    G) inserting a front end (31) of the surgical tool (10) into a depression (32) provided on the docking station (2), where a position of a bottom of the depression (32) with respect to the marking indicators (9) on the docking station (2) is known; and
    H) determining the spatial position of the front end (31) of the surgical tool (10) from the measured positions of the marking indicators (9) fastened to the docking station (2) and to the surgical tool (10) through the computer (16).

* * * * *